United States Patent [19]

Hooven

[11] Patent Number: 4,705,499

[45] Date of Patent: Nov. 10, 1987

[54] IMPLANTABLE SERVO VALVE HAVING INTEGRAL PRESSURE SENSOR

[75] Inventor: Michael D. Hooven, Miami, Fla.

[73] Assignee: Cordis Corporation, Miami, Fla.

[21] Appl. No.: 812,813

[22] Filed: Dec. 23, 1985

[51] Int. Cl.⁴ .......................................... A61M 27/00
[52] U.S. Cl. ........................................ 604/9; 128/748; 137/510
[58] Field of Search ........................... 137/508, 510; 604/8–10, 247; 128/748

[56] References Cited

U.S. PATENT DOCUMENTS 3,782,410  1/1974  Stueby ........................... 137/588 X
3,886,948  6/1975  Hakim ................................ 604/9
4,106,510  8/1978  Hakim et al. ........................ 604/9
4,557,721 12/1985  Hooven ............................... 604/9

Primary Examiner—Dalton L. Truluck
Attorney, Agent, or Firm—Lockwood, Alex, FitzGibbon & Cummings

[57] ABSTRACT

An implantable valve for allowing the passage of cerebrospinal fluid (CSF) from a ventricle of the brain of a patient to a suitable drainage location in the body of the patient includes a movable diaphragm having one of its sides in contact with dura mater and its other side in pressure communication with the drainage location. A valve assembly, actuated by movement of the diaphragm in response to increased epidural pressure, controls passage of CSF from the ventricle to the drainage location.

16 Claims, 8 Drawing Figures

IMPLANTABLE SERVO VALVE HAVING INTEGRAL PRESSURE SENSOR

BACKGROUND OF THE INVENTION

The present invention relates to an intracranial pressure relief valve and, more particularly, to a pressure relief valve for shunting excess cerebrospinal fluid (CSF) from a ventricle in the brain to another location in the body of patient when epidural pressure exceeds a predetermined level.

Hydrocephalus is a condition in which the body, for any one of a variety of reasons, is unable to relieve itself of CSF which collects in the ventricles of the brain. The excessive collection of CSF in the ventricular spaces results in an increase of both epidural and intradural pressures which, in turn, causes a number of adverse pysiological effects including compression of brain tissue, impairment of blood flow in the brain tissue and impairment of the brain's normal metabolism.

Hydrocephalus is frequently treated by draining CSF in order to relieve abnormally high intracranial pressure. A variety of CSF pressure relief valves and methods of controlling CSF pressure have been developed and include various forms of check valves, servo valves or combinations thereof. Such valves generally serve to divert CSF from the ventricles of the brain through a discharge line to some suitable drainage area in the body, such as the venous system or the peritoneal cavity.

Check valves operate by simply opening when the CSF pressure differential across the valve exceeds a predetermined thresold value. Servo valves, as used in the treatment of hydrocephalus, sense intracranial pressure and open as necessary to maintain the intracranial pressure within pre-established limits.

In one CSF servo valve, described in U.S. Pat. No. 4,557,721 of the present inventor, a flexible fluid-filled bladder, hydraulically coupled to a chamber defined in part by a flexible diaphragm, was inserted into the epidural space. Changes in epidural pressure resulted in movement of the diaphragm which, in turn, controlled passage of CSF through the valve as required to maintain a desired epidural pressure.

The present invention is directed to an improved implantable servo valve for the treatment of hydrocephalus. In contrast with prior valves, the improved valve eliminates the need for a separate fluid filled bladder and instead includes an integral movable surface which directly contacts the dura-mater of the patient when the valve is installed in a burr hole through the skull.

In view of the foregoing, it is a general object of the present invention to provide a new and improved pressure regulator valve for relieving intracranial pressure caused by the excessive accumulation of CSF in the brain ventricles.

It is a more specific object of the present invention to provide a CSF pressure regulator valve which eliminates the need for a separate pressure sensor bladder.

SUMMARY OF THE INVENTION

A cerebrospinal fluid pressure relief valve for subcutaneous implantation through a burr hole in the skull of a patient and responsive to pressure deformation of the underlying dura mater for controlling the flow of fluid from an associated ventricular location to a drainage location, includes a housing dimensioned to extend through the burr hole and defining an interior chamber open at one end and closed at the other end. A flexible diaphragm extends over and closes the open end of the chamber, and is arranged for engagement and movement with the underlying dura mater. Partition means form within the interior chamber an inlet chamber and an outlet chamber, and a passageway providing fluid communication therebetween. Inlet port means provide fluid communication between the ventricular location and the inlet chamber, and outlet port means provide fluid communication between the outlet chamber and the drainage location. Valving means operatively connected to the diaphragm control fluid flow through the passageway, the valving means increasing flow through the passageway in response to increased deflection of the diaphragm, and decreasing flow in response to decreased deflection, to relieve excessive fluid pressure at the ventricular location.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
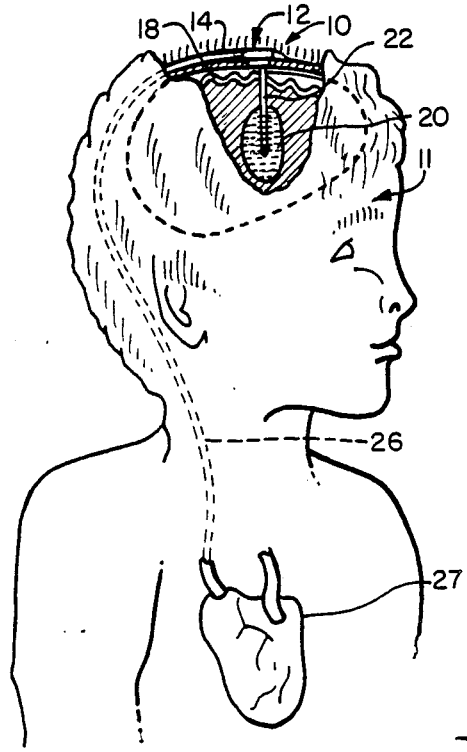
FIG. 1 is a perspective view, partially in section, of a CSF pressure relief system employing a servo valve constructed in accordance with the invention, showing such a system implanted within a patient.
Figure 2:
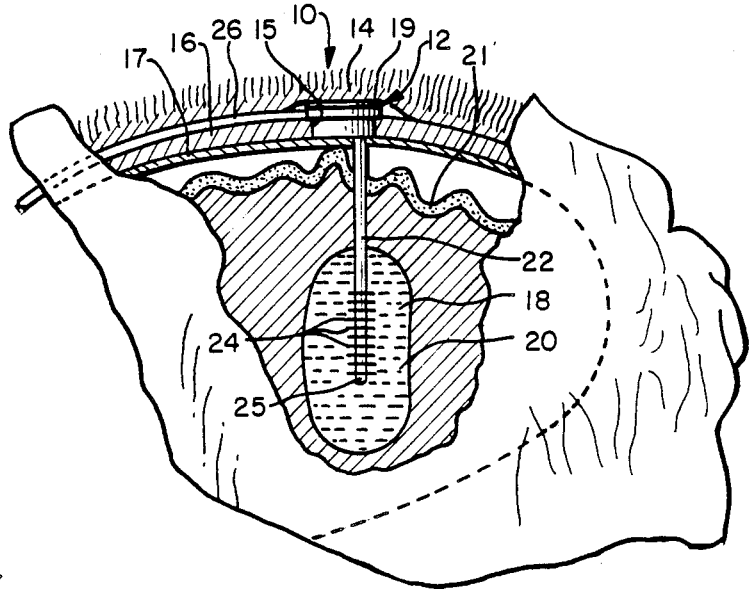
FIG. 2 is an enlarged perspective view, partially in section, of the pressure relief system illustrated in FIG. 1 showing the principal elements thereof.

Referring to the drawings, and in particular to FIGS. 1 and 2, a cerebrospinal fluid (CSF) pressure relief system 10 for maintaining a desired predetermined intracranial pressure in a patient 11 is illustrated.

The system shown includes a servo valve 12 constructed in accordance with the present invention for maintaining the desired intracranial pressure. Servo valve 12 is subcutaneously implanted beneath the scalp 14 and is received in a burr hole 15 formed through the skull 16 of the patient at the time of implantation. When implanted, the lower surface of valve 12 rests against the dura mater 17. An annular flange 19 formed adjacent the upper end of the valve limits its downward travel through burr hole 15.

CSF 18 is drained from a ventricle 20 of the brain 21 by means of a ventricular catheter 22. Catheter 22 is preferably radio-opaque in order to facilitate its accurate placement within the brain. A plurality of apertures 24 in the distal end 25 of catheter 22 permits CSF to pass to the interior of the catheter. At its other end, the ventricular catheter 22 passes through the dura mater 17 and connects to the servo valve 12.

Servo valve 12 is also connected to one end of a subcutaneously implanted drain catheter 26, the opposite end of which discharges into an appropriate location in the patient's body, such as, for example, the right atrium of the heart 27. Another drainage location, such as the peritoneal cavity, could be selected instead.

Regulator servo valve 12 regulates the flow of CSF from the brain ventricles to the selected discharge location as required to maintain a preselected epidural pressure. Increasing intracranial pressure is sensed at the lower surface of valve 12 and results in increased CSF flow through the valve such that epidural pressure remains relatively constant.

Figure 3:
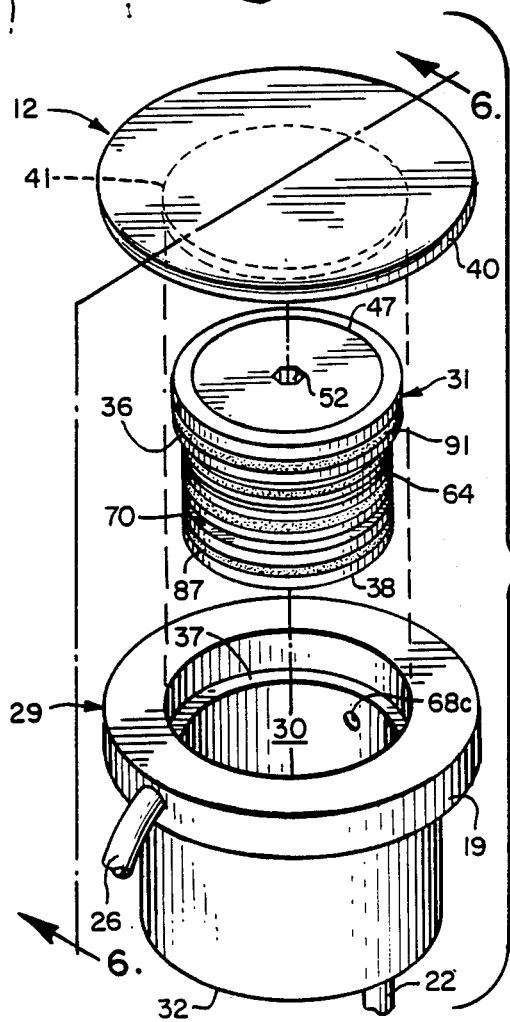
FIG. 3 is an enlarged, exploded, perspective view of the valve shown in FIGS. 1 and 2.
Figure 4:
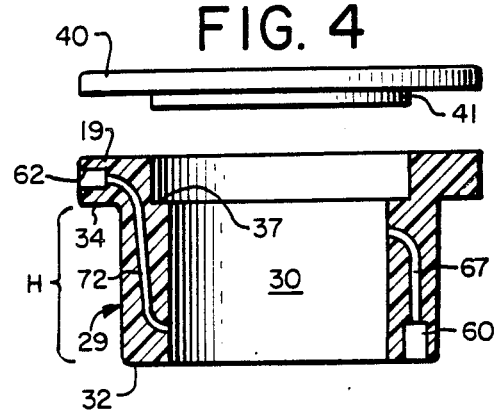
FIG. 4 is a cross-sectional view of a valve adapter sleeve constructed in accordance with one aspect of the invention.
Figure 5:
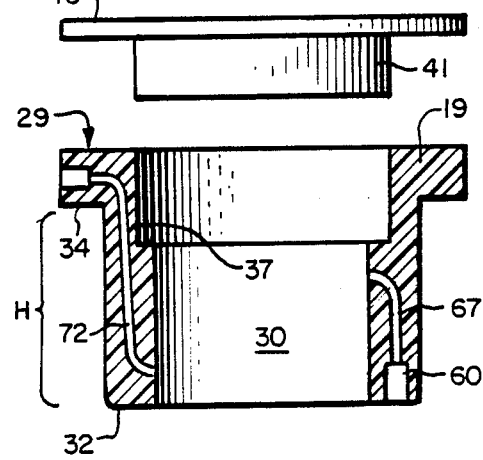
FIG. 5 is a cross-sectional view of another adapter sleeve similar to the sleeve shown in FIG. 4.

As illustrated in FIGS. 3-5, servo valve 12 comprises a circular hollow adaptor sleeve 29 having an interior region 30 dimensioned to receive a valve assembly insert 31. Flange 19 is integrally formed on the exterior surface of the sleeve adjacent the upper end thereof. The valve insert assembly 31 contains the operative elements of the servo valve, while adaptor sleeve 29 permits a single valve assembly insert construction to be used for most patient applications despite variations in skull thickness from individual to individual. Sleeve 29 is simple in construction and can be economically manufactured in a variety of sizes while insert 31, containing the more complex elements of the valve, is manufactured in relatively few different sizes in order to obtain the economic benefits of large scale production.

Sleeve 29 comprises a circular tubular member formed of a suitable, durable, biologically compatible material such as thermoplastic polymers of polyethersulfone or polycarbonates. Preferably, the vertical distance H (FIGS. 4 and 5) between the lower surface 32 of sleeve 29 and the lower surface 34 of flange 19 closely matches the thickness of the skull 16 (FIG. 2). The sleeve illustrated in FIG. 4 is suitable for use when the skull is relatively thin and accordingly, distance H is relatively short. The sleeve shown in FIG. 5, having a relatively longer dimension H, is appropriate for use when the skull is of greater thickness.

Valve assembly insert 31 comprises a generally cylindrical structure dimensioned to be received in the hollow interior region 30 of sleeve 29. The insert 31 includes a flange 36 adjacent its uppermost end which cooperates with a ledge 37 formed in interior region 30 to fix the vertical position of the insert within sleeve 29. In all cases, it is desired that the lower surface 38 of insert 31 be coplanar with the lower sleeve surface 32. Although dimension H will vary according to the thickness of a particular skull, the vertical distance between surface 32 and ledge 37 will remain constant.

To provide the assembled servo valve 12 with a smooth upper surface, sleeve 29 includes a circular removable cover 40. The diameter of cover 40 matches that of annular flange 19 and includes a center region 41 projecting downwardly from its lower surface. The diameter of region 41 matches that of interior region 30 while its vertical dimension is sufficient to completely fill the space above valve insert 31 when the insert is installed in sleeve 29.

Figure 6:
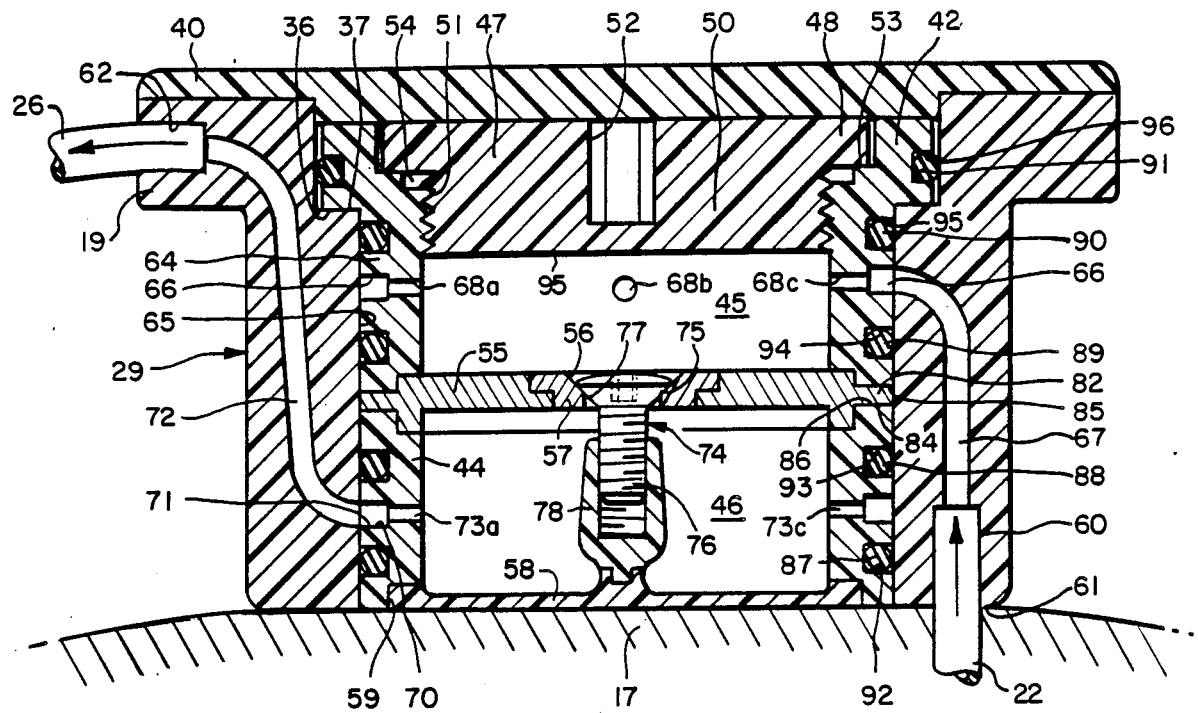
FIG. 6 is an enlarged cross-sectional view of the valve illustrated in FIG. 1 showing the valve in a closed position.
Figure 7:
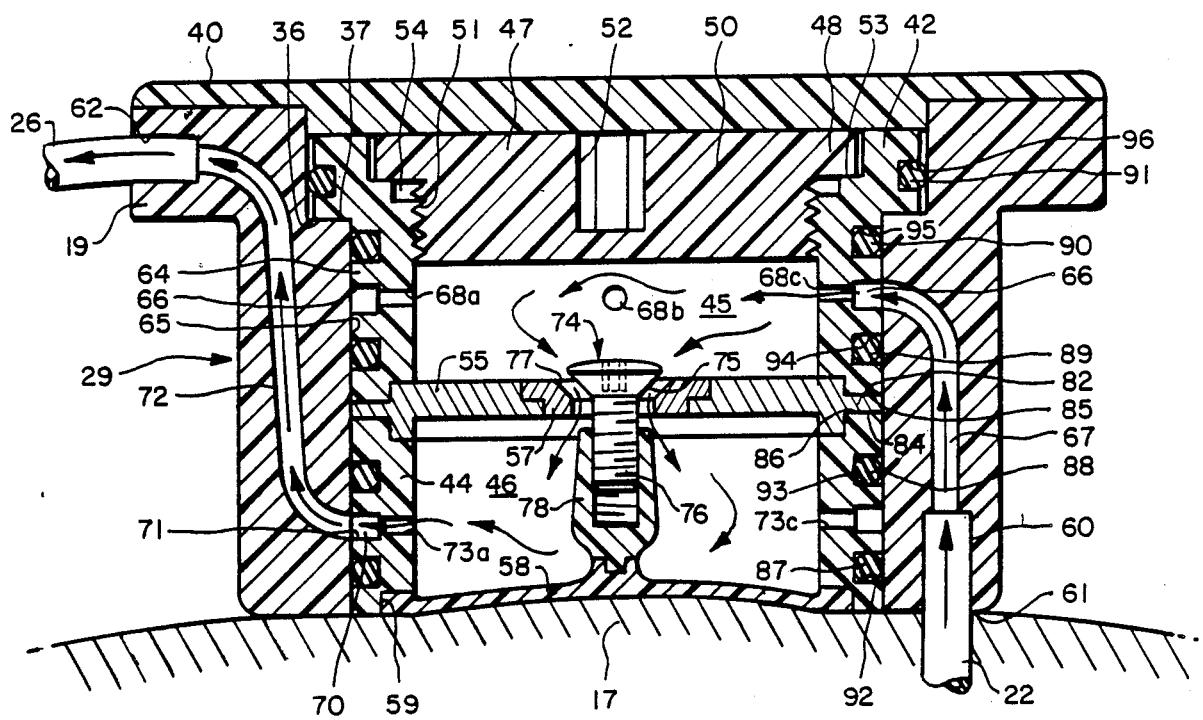
FIG. 7 is an enlarged cross-sectional view similar to FIG. 6 showing the valve in an open position.
Figure 8:
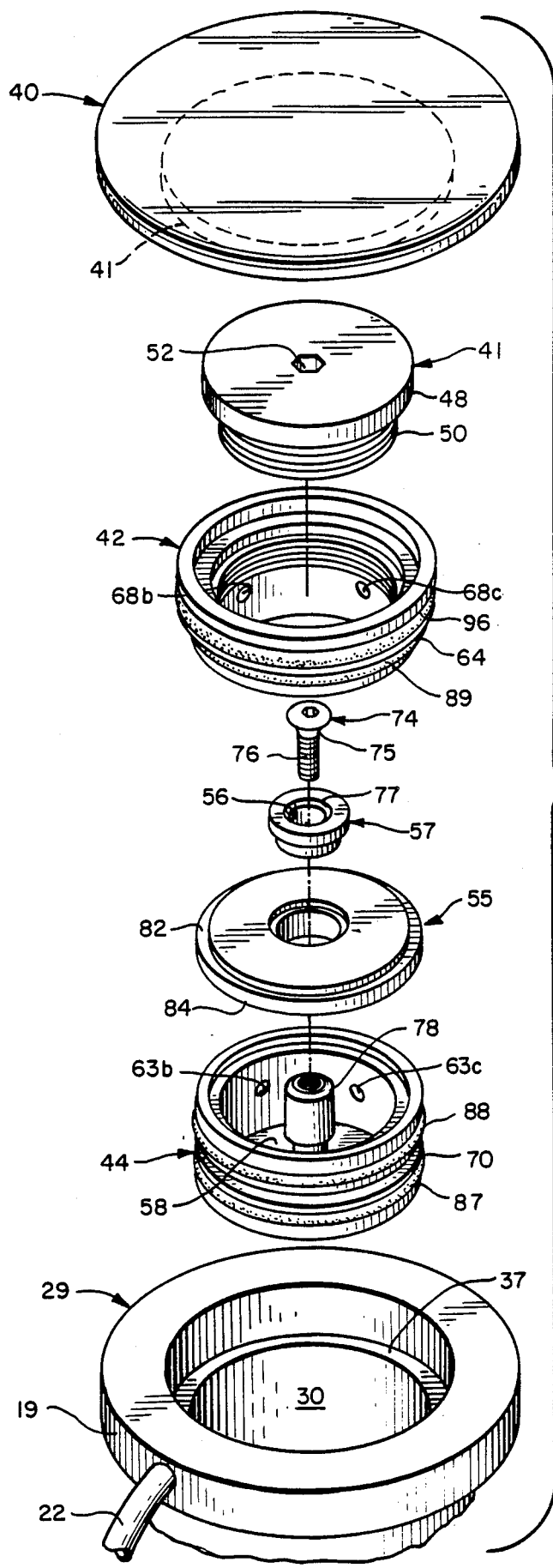
FIG. 8 is an enlarged, exploded, perspective view of the valve illustrated in FIG. 1 showing the principal elements of a valve assembly insert constructed in accordance with one aspect of the present invention.

The internal construction and operation of servo valve 12 may best be understood by reference to FIGS. 6, 7 and 8. Adjacent the uppermost end of the sleeve, the diameter of the interior region 30 is increased to form ledge 37. Valve assembly insert 31 comprises two generally cylindrical hollow upper and lower housing members 42 and 44 which are also formed of a durable, bio-compatible material. Flange 36 is formed on the exterior surface of upper housing member 42 adjacent its uppermost end.

Housing members 42 and 44 are each generally tubular in form and accordingly define input and output chambers 45 and 46 respectively. Input chamber 45 is bounded at its upper end by a removable cap 47. Cap 47 is generally cylindrical in form and includes a region 48 of relatively larger diameter positioned over a region of relatively smaller diameter 50. Smaller diameter region 50 is externally threaded while upper housing member 42 is provided with a set of complementary threads 51 adjacent its upper end. A hexagonal cross-sectioned recess 52 in the upper surface of the cap receives a tool (not shown) by means of which removable cap 47 can be engagingly or disengagingly rotated relative to upper housing member 42.

To effectively seal the upper end of upper housing member 42, an annular ledge 53 is formed adjacent its upper end which contacts the lower surface of region 48 when cap 47 is turned fully into upper housing member 42. A gasket 54, may be provided under ledge 53 to improve the seal.

The lower boundary of input chamber 45 is defined by a generally disc-shaped partition 55 which also defines the upper boundary of output chamber 46. An aperture 56 through partition 55 provides fluid communication between the input and output chambers.

Preferably, aperture 56 is defined by a unitary valve seat member 57, formed of saphire or similar rigid biocompatible material, which is mounted in partition 55.

The lower boundary of output chamber 46 is defined by a flexible, movable diaphragm 58 formed of a suitable bio-compatible material such as silicon rubber. As illustrated, diaphragm 58 extends fully across the open lower end of lower housing member 44 and is received in an annular channel 59 formed in the lower edge thereof. Alternatively, diaphragm 57 may be molded as an integral element of lower housing member 44 at the time of its manufacture.

An input port 60 is provided in the lower edge 61 of sleeve 29 for connection to ventricular catheter 22. An output port 62 in the outer vertical side wall of flange 19 connects to drain catheter 26.

A groove 64 in the outer surface of upper housing member 42 cooperates with the inner side wall 65 of sleeve 29 to define a hollow annular passage 66 around valve assembly insert 31 when it is installed in the sleeve. An input conduit 67, internally formed in sleeve 29, provides fluid communication between input port 60 and chamber 66. A plurality of radially directed apertures 68a–68c through the side wall of upper housing member 42 connect input chamber 45 with passage 66 to permit CSF from ventricle 20 (FIG. 1) to pass into the input chamber.

A similar groove 70, in the outer surface of lower housing member 44, together with side wall 65, defines a second annular passage 71 interconnected to output port 62 by means of a drain conduit 72 internally formed in sleeve 29. Radially directed apertures 74a 74b (FIG. 8) and 74c through lower housing member 44 permit CSF to pass from output chamber 46, through drain conduit 72 and output port 62, to drain catheter 26.

To regulate the passage of CSF through aperture 56, the servo valve 12 includes a generally cylindrical valve closure stem 74. Adjacent one end, the diameter of valve closure stem 74 progressively increases to form a frusto-conical ramped surface 75. At its other end 76, the stem is of uniform diameter and is externally threaded. The side walls of aperture 56 are bevelled as illustrated to form a valve seat 77 in valve seat member 57. Threaded end 76 extends downwardly through aperture 56 and into output chamber 46 while ramped surface 75 and valve seat 77 prevent the valve closure stem 74 from passing fully through the aperture.

Diaphragm 58 is provided with an upwardly projecting, internally threaded pillar 78 at its center which receives and engages the threaded end of valve stem 74. Preferably, pillar 78 is formed of a rigid material such as that used on construction of housing members 42 and 44. Because of the inherent resiliency of diaphragm 57, valve stem 74 will be pulled downwardly causing ramped surface 75 to engage valve seat 77 and thereby occlude aperture 56. Valve stem 74 can be engagingly or disengagingly rotated relative to diaphragm 57 to vary the contact force between ramped surface 75 and valve seat 77. To this end, the upper surface of the valve stem is provided with a hexagonally cross-sectioned recess for receiving an adjustment tool (not shown). To increase its flexibility, diaphragm 58 may include a convolution (not shown) in its operative surface.

To facilitate assembly of the valve assembly insert 31, the thickness of partition 55 can be reduced to form a step 82 in its upper surface adjacent its periphery. A similar step 84 is formed in the lower surface of the partition. The lower edge surface 85 of upper housing member 42 and the upper edge surface 86 of lower housing member 44 ar each shaped to interlock with the partition.

To prevent undesired leakage of CSF between valve assembly insert 31 and inner side wall 65, the insert is provided with a plurality of O-rings 87-91 each received in a respective channel 92-96 formed in the outer surface of valve assembly insert 31.

Although the operation of the regulator servo valve of the present invention should be clear from the foregoing description, a preferred operation of the valve will be described. When servo valve 12 is properly implanted, the lower surface of diaphragm 58 rests against the dura mater 17 (FIG. 2) and hence is subjected to deformation by the existing epidural pressure.

When the valve is thus installed, CSF from ventricle 20 fills input chamber 45. If epidural pressure is within normal limits, diaphragm 58 assumes the undeflected position shown in FIG. 6. Ramped surface 75 engages valve seat 77 to prevent the passage of CSF from input chamber 45 through aperture 56. When epidural pressure rises, diaphragm 57 is upwardly deflected to the position shown in FIG. 7 to raise valve stem 74 above valve seat 77 and thereby permit the passage of CSF through aperture 56.

The movement of diaphragm 58 is a function of the contact force between valve stem 74 and valve seat 77, the CSF fluid pressure in input chamber 45, the fluid pressure in output chamber 46 and the epidural pressure exerted on the lower surface of the diaphragm. To minimize the influence of ventricular CSF pressure on valve operation, the exposed upper surface area of valve stem 74 in input chamber 45 is preferably minimized.

With the influence of CSF pressure in input chamber 45 minimized, the position of diaphragm 58 is determined primarily by the difference between the epidural pressure and the pressure of the fluid in output chamber 46. The contact force between the valve stem 74 and valve seat 77 pre-stresses diaphragm 58 to establish a pressure threshold which the pressure differential across the diaphragm must exceed before the stem lifts clear of the seat. This contact force can be adjusted by rotating the valve stem to alter the pressure/flow characteristics of the valve as necessary to suit the specific requirements of individual patients. Since the epidural pressure will never exceed the ventricular CSF pressure, backflow of fluid between output chamber 46 and input chamber 45 should never occur. An abnormal increase of fluid pressure in output chamber 46 will deflect diaphragm 58 downwardly, resulting in closure of the valve.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A cerebrospinal fluid pressure relief valve for subcutaneous implantation through a burr hole in the skull of a patient and responsive to pressure deformation of the underlying dura mater for controlling the flow of fluid from an associated ventricular location to a drainage location, comprising:
   a housing dimensioned to extend through the burr hole and defining an interior chamber open at one end and closed at the other end;
   a flexible diaphragm extending over and closing the open end of said chamber, said diaphragm being arranged for engagement and movement with the underlying dura mater;
   partition means form within said interior chamber an inlet chamber and an outlet chamber, and a passageway providing fluid communication therebetween;
   inlet port means providing fluid communication between the ventricular location and said inlet chamber;
   outlet port means providing fluid communication between said outlet chamber and the drainage location; and
   valving means operatively connected to said diaphragm controlling fluid flow through said passageway, said valving means increasing flow through said passageway in response to increased deflection of said diaphragm, and decreasing flow in response to decreased deflection, to relieve excessive fluid pressure at the ventricular location.

2. A pressure relief valve as defined in claim 1 wherein said housing is cylindrical and has a diameter less than the diameter of the burr hole.

3. A pressure relief valve as defined in claim 2 wherein said housing includes at said closed end a flange portion having a diameter greater than the diameter of the burr hole.

4. A pressure relief valve as defined in claim 3 wherein said housing includes a sleeve portion and a body portion, said sleeve portion including said flange portion and said body portion including said interior chamber and fitting within said sleeve portion, and said sleeve portion is dimensioned so as to extend through the burr hole to position the open end of said body portion in contact with the underlying dura mater when said flange portion is positioned against the skull.

5. A pressure relief valve as defined in claim 1 wherein said flexible diaphragm is formed of a silicon rubber.

6. A pressure relief valve as defined in claim 1 wherein said partition means comprise a partition member extending across said interior chamber, and said partition member includes an aperture defining said passageway.

7. A pressure relief valve as defined in claim 6 wherein said valving means comprise a valve stem extending through said aperture to partially occlude said passageway.

8. A pressure relief valve as defined in claim 7 wherein said valve stem is movable along the axis of said passageway and is tapered to open said passageway with increased deflection of said diaphragm.

9. A pressure relief valve as defined in claim 8 wherein said valve stem member is mounted to said diaphragm for movement therewith.

10. A pressure relief valve as defined in claim 9 including adjustment means for adjusting the position of said valve stem relative to said diaphragm to set the pressure at which the valve opens.

11. A pressure relief valve as defined in claim 10 wherein said valve stem is threadably mounted to said diaphragm, and said closed end of said housing includes a removable cap to provide for rotation of said valve stem from the exterior of said housing.

12. A cerebrospinal fluid pressure relief valve for subcutaneous implantation through a burr hole in the skull of a patient and responsive to pressure deformation of the underlying dura mater for controlling the flow of fluid from an associated ventricular location to a drainage location, comprising:

a cylindrical housing dimensioned to extend through the burr hole and defining an interior chamber open at one end and closed at the other end;

a flexible diaphragm extending over and closing the open end of said chamber, said diaphragm being arranged for engagement and movement with the underlying dura mater;

a disc-shaped partition extending across said interior chamber for dividing said chamber into an inlet chamber and an outlet chamber, said partition including a central aperture forming a fluid passageway between said inlet and outlet chambers;

inlet port means providing fluid communication between the ventricular location and said inlet chamber;

outlet port means providing fluid communication between said outlet chamber and the drainage location; and a valve stem mounted to said diaphragm for movement therewith and extending through said passageway for increasingly opening said passageway with increased deflection of said diaphragm to relieve excessive pressure at the ventricular location.

13. A pressure relief valve as defined in claim 12 wherein said flexible diaphragm is formed of a silicon rubber.

14. A pressure relief valve as defined in claim 12 including adjustment means for adjusting the position of said valve stem relative to said diaphragm to set the pressure at which the valve opens.

15. A pressure relief valve as defined in claim 14 wherein said valve stem is threadably mounted to said diaphragm, and said closed end of said housing includes a removable cap to provide for rotation of said valve stem from the exterior of said housing.

16. A pressure relief valve as defined in claim 12 wherein said housing includes a sleeve portion and a body portion, said sleeve portion including said flange portion and said body portion including said interior chamber and fitting within said sleeve portion, and said sleeve portion is dimensioned so as to extend through the burr hole and position the open end of said body portion in contact with the underlying dura mata when said flange portion is positioned against the skull.

* * * * *